(12) United States Patent
Hoelscher et al.

(10) Patent No.: US 11,420,921 B2
(45) Date of Patent: Aug. 23, 2022

(54) 2-(5-ISOPROPYL-2-METHYL-CYCLOHEX-2-EN-1-YL-)ACETALDEHYDE AND 2-(6-ISOPROPYL-3-METHYL-CYCLOHEX-2-EN-1-YL-) ACETALDEHYDE AS NEW ODORANTS

(71) Applicant: SYMRISE AG, Holzminden (DE)

(72) Inventors: Bernd Hoelscher, Halle (DE); Frank Gerstmann, Frankfurt Am Main (DE); Mark Mansfeld, Brevörde (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 17/276,442

(22) PCT Filed: Sep. 19, 2018

(86) PCT No.: PCT/EP2018/075387
§ 371 (c)(1),
(2) Date: Mar. 15, 2021

(87) PCT Pub. No.: WO2020/057741
PCT Pub. Date: Mar. 26, 2020

(65) Prior Publication Data
US 2022/0033338 A1    Feb. 3, 2022

(51) Int. Cl.
*C07C 47/225* (2006.01)
*A61K 8/33* (2006.01)
*A61Q 13/00* (2006.01)
*C11B 9/00* (2006.01)

(52) U.S. Cl.
CPC .............. *C07C 47/225* (2013.01); *A61K 8/33* (2013.01); *A61Q 13/00* (2013.01); *C11B 9/0034* (2013.01); *A61K 2800/591* (2013.01)

(58) Field of Classification Search
CPC ................................ C07C 47/225; A61K 8/33
See application file for complete search history.

(56) References Cited

U.S. PATENT DOCUMENTS

2013/0090390 A1    4/2013  Singer et al.

FOREIGN PATENT DOCUMENTS

| DE | 10114176 A1 | 9/2002 |
| EP | 1 054 053 A2 | 11/2000 |
| EP | 2 578 671 A1 | 4/2013 |
| WO | WO-2017/046071 A1 | 3/2017 |

OTHER PUBLICATIONS

Arctander, *Perfume and Flavor Chemicals: (aroma Chemicals)*. Montclair, N.J, 1969. Table of contents only from 1994 reprint.
Bauer et al., "Common Fragrance and Flavor Materials: Preparation, Properties, and Uses," Weinheim: WILEY-VCH, 2001. Table of Contents only. Internet resource: https://onlinelibrary.wiley.com/doi/book/10.1002/3527600205.
Coulomb, J. "Beyond muguet." *Perfumer & Flavorist* 43(4) (2018): 40-46.
Goeke, A. "KP Discovery of Nympheal: The definite muguet aldehyde." *Perfum. Flavor* 43(3) (2018): 24-40.
International Search Report and Written Opinion for Application No. PCT/EP2018/075387, dated May 22, 2019.
Klein et al., "Der stereochemische verlauf der alkalischen epoxydation von α, β-ungesättigten carbonylverbindungen der cyclischen monoterpenreihe." *Tetrahedron* 19(6) (1963): 1091-1099. English-language abstract only.
Thomas et al., "Addition of a Functionalized Isoprene Unit to an Allyl Alcohol. III. The reaction with optically active cis☐carveol." *Helvetica Chimica Acta* 53(5) (1970): 1145-1151.
Genva et al., "Is It Possible to Predict the Odor of a Molecule on the Basis of its Structure?", Int. J. Mol. Sci. 20(3018):16 pages (2019).

*Primary Examiner* — Arrie L Reuther
(74) *Attorney, Agent, or Firm* — Marshall, Gerstein & Borun LLP

(57) ABSTRACT

The present invention relates to novel compounds of formula (I)

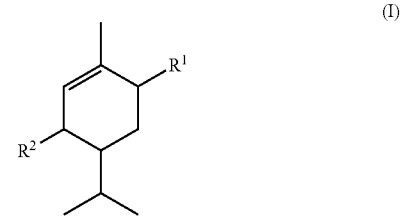

as well as mixtures comprising or consisting of compounds of formula (I). Furthermore, the present invention relates to a process for the preparation of the compounds of formula (I) and to the use of the compounds of formula (I) as a perfuming ingredient, in particular as a lily of the valley perfuming ingredient. Ultimately, the present invention relates to perfume preparations and perfumed products or consumer goods comprising at least one of the compounds of formula (I).

20 Claims, No Drawings

2-(5-ISOPROPYL-2-METHYL-CYCLOHEX-2-EN-1-YL-)ACETALDEHYDE AND 2-(6-ISOPROPYL-3-METHYL-CYCLOHEX-2-EN-1-YL-) ACETALDEHYDE AS NEW ODORANTS

CROSS-REFERENCE TO RELATED APPLICATIONS

This is a U.S. National Phase of International Application No. PCT/EP2018/075387, filed Sep. 19, 2018, the content of which is incorporated herein by reference.

FIELD OF INVENTION

The present invention relates to novel compounds of formula (I)

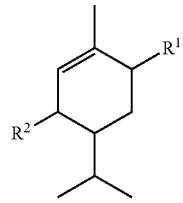

(I)

as well as mixtures comprising or consisting of compounds of formula (I). Furthermore, the present invention relates to a process for the preparation of the compounds of formula (I) and to the use of the compounds of formula (I) as a perfuming ingredient, in particular as a lily-of-the-valley perfuming ingredient. Ultimately, the present invention relates to perfume preparations and perfumed products or consumer goods comprising at least one of the compounds of formula (I).

STATE OF THE ART

Compounds with a floral odor are an indispensable component in the fragrance industry and in the manufacture of perfumes, cosmetics, personal care products as well as detergents, cleaning agents and other consumer goods. Despite a large number of existing fragrances, there is still a great demand from the perfumery industry for new floral fragrances, especially lily of the valley olfactory notes, which enable an expansion of the perfumery palette. Lily of the valley olfactory notes are among the popular olfactory notes and are very often used in perfumes and fragrance blends. Extensive review articles on the historical development of lily of the valley fragrances can be found in A. Goeke, P. Kraft, D. Lelievre, Perfumer & Flavorist, 2018, 43(3), 24 and J. Coulomb, Perfumer & Flavorist, 2018, 43 (4), 40.

Aldehydic cyclohexenes have been described in the literature as fragrances. EP 1 054 053 A1 describes tert-butyl-substituted cyclohexenes that smell like lily of the valley. While compound (A) smells aldehydic, floral, like lily of the valley and greasy, the methyl-substituted compound (B) is characterized by white floral odor notes in addition to lily of the valley.

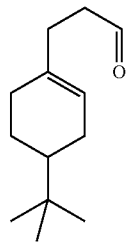

(A)

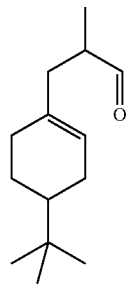

(B)

EP 2 578 671 A1 describes fragrances with a strong green, watery and floral odor reminiscent of lily of the valley.

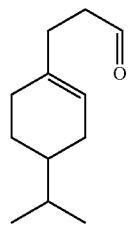

(C)

WO 2017046071 A1 also describes cyclohexenes with green and floral odor notes.

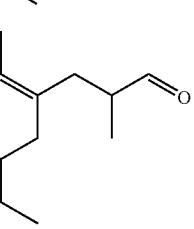

(D)

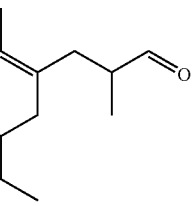

(E)

All the cyclohexenes described (A) to (E) have in common that they have a propanal substituent. The syntheses are multi-step and in some cases proceed under moderate yields. In addition, the synthesis of these compounds proceeds via cyclohexene derivatives with an exo-positional double bond, which are chemically complex to prepare selectively.

Very high demands are placed on new fragrances: In addition to their primary properties, namely odor, they should have additional positive secondary properties, such as greater stability under certain conditions of use, higher substantivity and/or diffusivity, or better adhesion. They are also said to exhibit very good biodegradability and to be dermatologically and toxicologically safe.

Fragrances characterized by the above-mentioned positive secondary properties enable increased effectiveness in the manufacture of fragrance preparations and perfumed products. For example, by using fragrances with a better sensory profile, higher substantivity and/or better adhesion, the number and input quantities of fragrances in corresponding formulations can be optimized and/or minimized, leading to sustainable resource conservation in the manufacture of perfumed products.

The primary task of the present invention was to provide new compounds with a floral odor note, in particular a lily of the valley odor note, that is, the compounds should impart an odor impression that largely corresponds to the complexity of the natural odor of the lily of the valley flower. In addition, these compounds should be equivalent or superior to prior art lily of the valley odorants in terms of their secondary properties. In addition, the new fragrance compounds should be attributable to renewable and natural starting materials, i.e., renewable raw materials.

Another object of the present invention relates to the preparation of such novel compounds.

An additional task relates to the provision of new compounds with a floral odor note, in particular a lily of the valley odor note, for use as fragrances or for the preparation of fragrance preparations, and perfumed products or consumer goods comprising at least one of these new compounds.

The tasks set are solved according to the invention by the objects of the independent patent claims. Further aspects and preferred embodiments of the present invention result from the wording of the dependent patent claims, the following description and the embodiment examples.

DETAILED DESCRIPTION OF THE INVENTION

The search for suitable substances with lily of the valley odor, which led to the present invention, was complicated by the following facts:

- the mechanisms of odor perception are not well understood; and
- the relationships between the specific odor perception on the one hand and the chemical structure of the associated odorant on the other hand have not been sufficiently researched.

Furthermore, even minor changes to the structural composition of a known odorant lead to major changes in sensory properties and impair its compatibility for the human organism.

The success of the search for suitable odorants therefore depends heavily on the intuition of the searcher.

A first object of the present invention relates to novel compounds of the general formula (I).

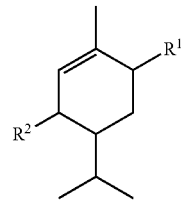

(I)

where the variable residues $R^1$ and $R^2$ have the following meaning:
$R^1$ stands for H or —$CH_2$—CHO, and
$R^2$ stands for H or —$CH_2$—CHO,
with the proviso that $R^1 \neq R^2$;
and stereoisomers or mixtures thereof.

In the context of the present invention, the term "compounds of formula (I)" is understood to mean both the individual compounds of formula (I) and all mixtures of the compounds of formula (I) in any mixing ratio. That is, statements in the following description concerning "compounds of formula (I)" apply both to a single compound of formula (I) and to mixtures consisting of or comprising compounds of formula (I) in any mixing ratio.

According to the invention and preferably, the compounds of formula (I) can be present in different forms, corresponding to the possible isomers, in particular the regio-isomers for R1 and R2 and/or the stereoisomers of formula (I), both individually and as mixtures.

In a preferred embodiment of the invention, a regio-isomer is a compound of formula (I), wherein R1 represents a —$CH_2$—CHO group and $R^2$ represents a hydrogen atom.

In another preferred embodiment of the invention, a further regioisomer is a compound of formula (I), wherein R1 represents a hydrogen atom and $R^2$ represents a —$CH_2$—CHO group.

The compounds of formula (I) according to the invention, as defined above, may also be present as stereoisomers. In the context of the present invention, the term stereoisomers includes all possible diastereomers or enantiomers of the compounds of formula (I).

Furthermore, the definition of the compounds of formula (I) also includes mixtures of the stereoisomers, in particular also the racemates or enantiomerically enriched mixtures, as well as their enantiomerically pure forms.

Surprisingly, it has been shown that the compounds of formula (I) impart an olfactory impression that is very close to the complexity of the natural odor of the lily of the valley flower. That is, the odor impression imparted by the compounds of formula (I) is characterized by outstanding naturalness and complexity, especially with respect to the lily of the valley odor note.

In addition, the present invention relates to a compound of formula (I) selected from the group consisting of the compounds of formula (II) and compounds of formula (III):

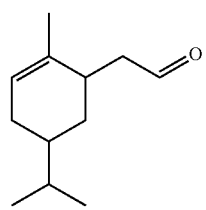

(II)

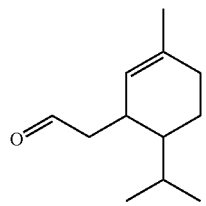

(III)

as well as their stereoisomers, in particular diastereomers or enantiomers, or mixtures thereof.

The compounds of formula (II) or formula (III) according to the invention may be designated as 2-(5-isopropyl-2-methyl-cyclohex-2-en-1-yl-)acetaldehyde or as 2-(6-isopropyl-3-methyl-cyclohex-2-en-1-yl-)acetaldehyde.

The compounds of the formula (II) or of the formula (III) according to the invention may be present individually or as mixtures of the aforementioned compounds of the formula (II) or of the formula (III).

The compounds of formula (II) are characterized by having in particular aldehydic, floral, green, dry and lily of the valley-like notes. The compounds of formula (III) are characterized in particular by having green, aldehydic and floral odor notes reminiscent of lily of the valley.

The compounds of formula (II) or formula (III) may be present in various forms corresponding to the possible stereoisomers, in particular enantiomers or diastereomers, of formula (II) or formula (III).

Furthermore, the definition of the compounds of formula (II) or formula (III) also includes mixtures of the stereoisomers, in particular also the racemates or enantiomerically enriched mixtures, as well as their enantiomerically pure forms.

In another preferred embodiment according to the first aspect, the present invention relates to compounds of formula (II) as represented by formula (IIa) or formula (IIb):

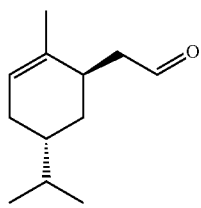

(IIa)

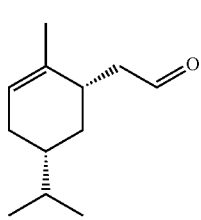

(IIb)

as well as their mixtures.

The enantiomerically pure compound of formula (IIa) exhibits in particular lily of the valley-like, floral and green notes. The enantiomerically pure compound of formula (IIb) exhibits, in particular, floral, green and aldehydic notes.

In another preferred embodiment, the present invention relates to compounds of formula (III) as represented by formula (IIIa) or formula (IIIb):

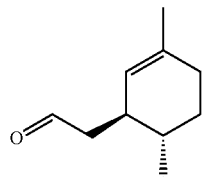

(IIIa)

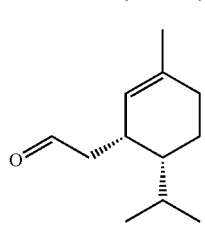

(IIIb)

as well as their mixtures.

In particular, the enantiomerically pure compound of formula (IIIa) exhibits aldehydic, green and floral notes reminiscent of lily of the valley.

In particular, the enantiomerically pure compound of formula (IIIb) exhibits green, floral, aldehydic and lily of the valley-like notes.

Preferably, the compounds of formula (IIa), formula (IIb), formula (IIIa) or formula (IIIb) according to the invention and described above are present as racemates, enantiomerically enriched mixtures or in their enantiomerically pure form.

In the present text, the term "compounds of formula (IIa)" or "compounds of formula (IIb)" or "compounds of formula (IIIa)" or "compounds of formula (IIIb)" covers both the individual compounds and all mixtures of the aforementioned compounds in any mixing ratio.

The term "compounds of formula (I)" covers both the individual compounds selected from the group consisting of the compounds of formula (II), compounds of formula (III), compounds of formula (IIa) or formula (IIb) and compounds of formula (IIIa) or formula (IIIb), as well as their stereoisomers, and all mixtures of the aforementioned compounds and their stereoisomers in any mixing ratio.

Surprisingly, the compounds according to the invention exhibit predominantly lily of the valley-like, floral and green notes.

The invention relates to the compounds according to the invention as such individually or also to mixtures of the compounds according to the invention.

Another object of the present invention thus relates to mixtures comprising compounds of formula (I), in particular (a) at least one compound of formula (II) or a stereoisomer thereof, as defined above, and (b) at least one compound of formula (III) or a stereoisomer thereof, as defined above, or consisting of compounds of formula (I), in particular (a) at least one compound of formula (II) or a stereoisomer thereof, as defined above, and (b) at least one compound of formula (III) or a stereoisomer thereof, as defined above.

Among the mixtures comprising or consisting of the compounds of formula (II), as defined above, and (ii) the compound of formula (III), as defined above, mixtures are preferred according to the invention with
  a mass ratio of the compound of the formula (II) to the compound of the formula (III) in the range from 0.01 to 99.99, preferably in the range from 0.1 to 99.9, preferably in the range from 0.5 to 99.5, preferably in the range from 1.0 to 99.0, preferably in the range from 1.5 to 98.5, preferably in the range from 2.0 to 98.0; and/or a total proportion of the compounds of the formulae (II) and (III) greater than 0.01% by weight, preferably greater than 1% by weight, preferably greater than 10% by weight, more preferably greater than 50% by weight, particularly preferably greater than 90% by weight, based on the total weight of the mixture comprising compound (II) and/or (III).

In another aspect of the present invention, the present invention also comprises preparation methods for preparing the compounds of formula (I), compounds of formula (II), and compounds of formula (III), wherein several alternative synthesis routes are possible.

The compounds of formula (I) or formula (II) according to the invention can be synthesized by the methods described in more detail below.

One possibility for the preparation of the compounds of formula (I) or formula (II) according to the invention is the acidic reaction of the known compound 2-methyl-5-(1-methylethyl-)2-cyclohexen-1-ol (IV) with vinyl ethers (R—O). The resulting acetals (V) undergo acid catalyzed cleavage to the vinyl ethers (VI), which are directly thermally converted to the desired aldehydes. The R radicals of the vinyl ether are selected from the group consisting of linear C1 to C20 alkyl radical, branched C1 to C20 alkyl radical, cyclopentyl radical and cyclohexyl radical.

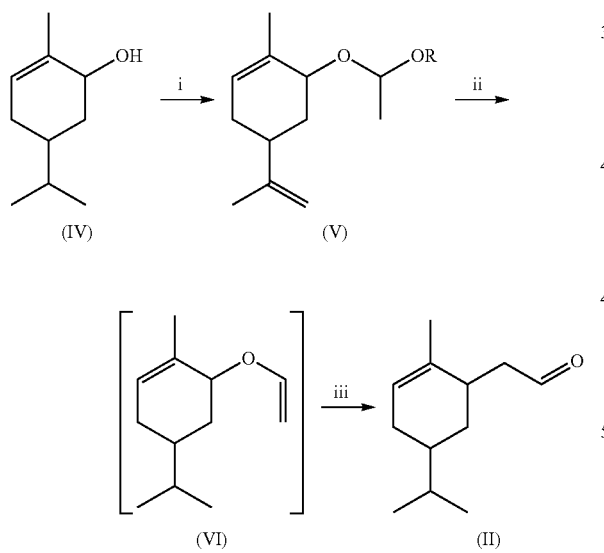

Another alternative possibility is the acidic conversion of the known and commercially available natural product 2-methyl-(1-methylethenyl-)2-cyclohexen-1-ol (VII) (E. Klein, G. Ohloff, Tetrahedron, 1963, 19, 1091; A. F. Thomas, G. Ohloff, Hel. Chim. Acta 1970, 53 (5), 1145) with vinyl ethers (R—O). The resulting acetals (VIII) undergo acid catalyzed cleavage to the vinyl ethers (IX), which are directly thermally converted to the aldehyde (X). Hydrogenation of the terminal double bond allows the desired aldehyde (II) to be obtained. The radicals R of the vinyl ether are selected from the group consisting of linear C1 to C20 alkyl radical, branched C1 to C20 alkyl radical, cyclopentyl radical and cyclohexyl radical.

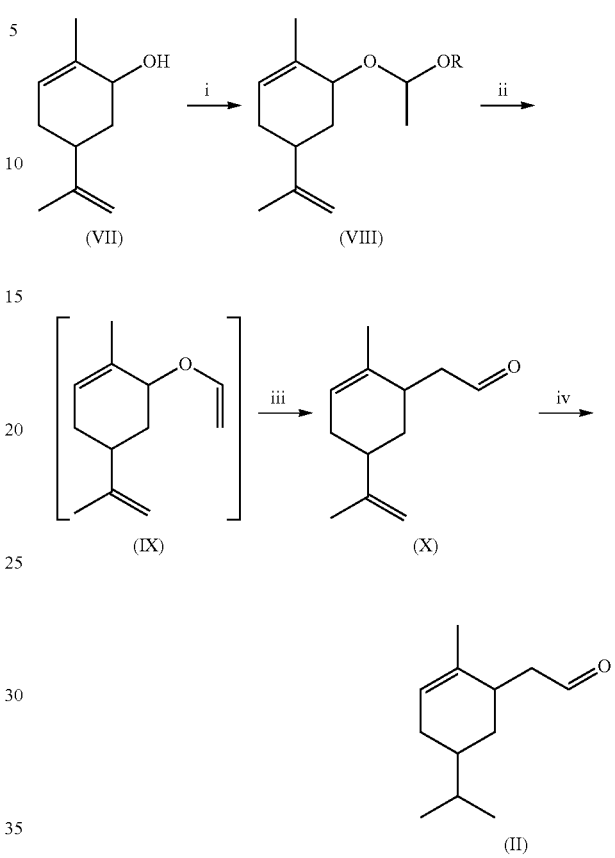

The compounds of formula (I) or formula (III) according to the invention can be synthesized by the methods described in more detail below.

One possibility for the preparation of the compounds of formula (I) or formula (III) according to the invention consists in the acidic reaction of the known natural product 1-methyl-4-(1-methylethyl-)2-cyclohexen-1-ol (XI) (E. Klein, G. Ohloff, Tetrahedron, 1963, 19, 1091; A. F. Thomas, G. Ohloff, Hel. Chim. Acta, 1970, 53 (5), 1145.) with vinyl ethers (R—O). The resulting acetals (XII) undergo acid catalyzed cleavage to the vinyl ethers (XIII), which are directly thermally converted to the desired aldehydes. The R radicals of the vinyl ether are selected from the group consisting of linear C1 to C20 alkyl radical, branched C1 to C20 alkyl radical, cyclopentyl radical and cyclohexyl radical.

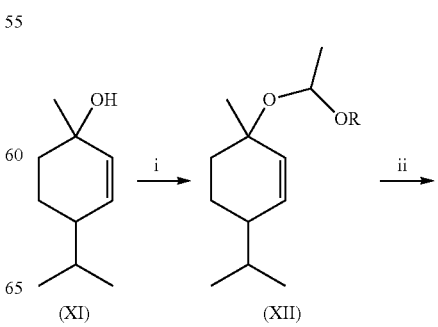

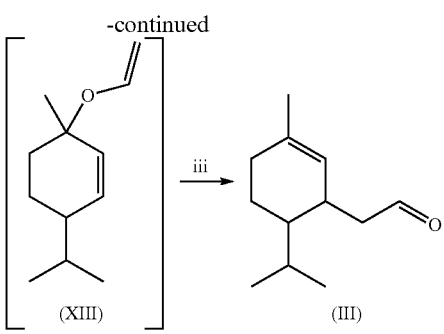

Another alternative possibility is the acidic reaction of the known compound 1-methyl-4-(1-methylethenyl-)2-cyclohexen-1-ol (XX) with vinyl ethers. The resulting acetals (XXI) undergo acid catalyzed cleavage to the vinyl ethers (XXII), which are directly thermally converted to the aldehyde (XXIII). Hydrogenation of the terminal double bond allows the preparation of the desired aldehyde (III). The R radicals of the vinyl ether are selected from the group consisting of linear C1 to C20 alkyl radical, branched C1 to C20 alkyl radical, cyclopentyl radical and cyclohexyl radical.

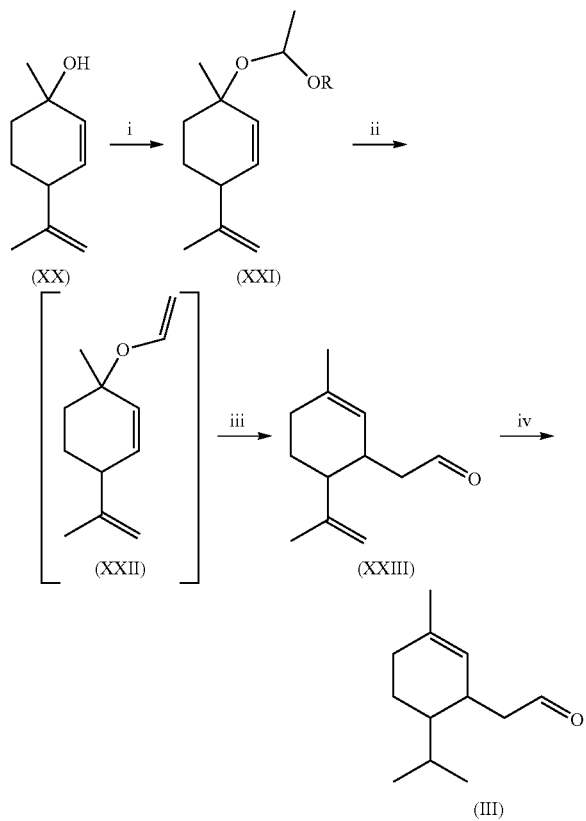

In step (i) of the processes according to the invention described above, the compounds of formulae (IV), (VII), (XI) and (XX) are converted into the acetals. For this purpose, Brønstedt acids or a Lewis acid are preferably used as catalyst.

In step (i) of the methods of the invention described above, the radicals R of the compounds of formulae (V), (VIII), (XII) and (XXI) are defined as preferably linear alkyl having a chain length of C1 to C20, branched alkyl having a chain length of C1 to C20, cyclopentyl or cyclohexyl.

Steps (ii) and (iii) of the processes of the invention described above are preferably carried out as a one-pot process. In this process, acid cleavage is carried out to give the vinyl ethers (VI), (IX), (XIII) and (XXII), followed by Claisen rearrangement to give the compounds (II), (III), (X) and (XXIII) at a temperature 150° C., preferably at a temperature in the range from 150 to 250° C., even more preferably at a temperature in the range from 160 to 180° C. Preferably, Brønstedt acids or Lewis acids are used as catalysts.

Steps (iv) of the processes according to the invention described above are carried out in the presence of hydrogen and a catalyst, for example palladium consumed on a support material, under the usual conditions. Advantageous support materials include: Activated carbon, carbon, aluminium oxides, metal oxides, silica gels, zeolites, clays, clay granules, amorphous aluminium silicates, or other inorganic supports. A preferred support material is activated carbon. A particularly preferred catalyst is palladium on activated carbon.

Furthermore, the present invention relates to the use of at least one of the compounds according to the invention, in particular the compounds of formulae (I), (II) or (III) described above or a stereoisomer thereof, or a mixture of the aforementioned compounds or stereoisomers thereof as a perfume, in particular as a lily of the valley perfume, or for the preparation of a perfume preparation, in particular with lily of the valley perfume.

Thus, another object of the present invention relates to a perfume preparation comprising at least one compound of formula (I), (II) or (III) or a stereoisomer thereof as defined above, preferably in a sensory effective amount.

In the context of the present invention, a fragrance preparation is a mixture of different substances which is produced from the corresponding substances according to a recipe or formulation in accordance with a predetermined process. Such preparations are specifically produced and used for the purpose of imparting, modifying or enhancing a desired odor impression which is usually perceived as pleasant or otherwise positive.

A perfume preparation according to the invention, in particular in the form of a perfume oil, preferably with a lily of the valley odor note, consists of or comprises at least one compound(s) according to the invention, in particular a compound of the formulae (I), (II) or (III) or a stereoisomer thereof, as defined above, and one, two, three, four, five, six, seven, eight, nine, ten or more further perfume(s) and/or aroma(s) which are not compound(s) of the formulae (I), (II) or (III).

In a preferred embodiment, the perfume preparation according to the invention comprises or consists of a compound of formula (II) and a compound of formula (III) or an isomer of these compounds.

By combining the compound(s) of formulae (I), (II) or (III) as defined above, preferably in one of the embodiments indicated as preferred, with one or more further fragrance(s) and/or aroma(s), interesting new fragrance preparations can be produced. In this way, mixtures with particularly interesting, natural, new and original notes can be created. Fragrances and/or flavoring substances which are suitable for use in a fragrance preparation according to the invention as further fragrances or flavoring substances in the sense of the above definition can be found, for example, in S. Arctander, Perfume and Flavor Materials, Vol. I and II, Montclair, N. J. 1969, self-published, or K. Bauer et al, Common Fragrance and Flavor Materials, 4th Edition, Wiley-VCH, Weinheim 2001.

The following are mentioned in detail:

Extracts from natural raw materials such as essential oils, concretes, absolutes, resins, resinoids, balsams, tinctures such as. Ambergris tincture; Amyris oil; *Angelica* seed oil; *Angelica* root oil; Anise oil; Valerian oil; Basil oil; Tree moss absolute; Bay oil; Mugwort oil; Benzoeresin; Bergamot oil; Beeswax absolute; Birch tar oil; Bitter almond oil; Savory oil; Bucco leaf oil; Cabreuva oil; Cade oil; Calmus oil; Camphor oil; *Cananga* oil; Cardamom oil; Cascarilla oil; *Cassia* oil; Cassie-absolue; Castoreum-absolue; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolute; Oak moss absolute; Elemi oil; Tarragon oil; *Eucalyptus citriodora* oil; *Eucalyptus* oil; Fennel oil; Spruce needle oil; *Galbanum* oil; *Galbanum* resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; Calamus oil; Chamomile oil blue; Chamomile oil Roman; Carrot seed oil; Cascarilla oil; Pine needle oil; Spearmint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; *Litsea cubeba* oil; Bay leaf oil; Macis oil; Marjoram oil; Mandarin oil; Masso bark oil; *Mimosa* absolue; Musk grain oil; Musk tincture; Muscat oil; Myrrh absolute; Myrrh oil; Myrtle oil; Clove leaf oil; Clove flower oil; Neroli oil; Olibanum absolute; Olibanum oil; Opopanax oil; Orange flower absolute; Orange oil; *Origanum* oil; Palmarosa oil; Patchouli oil; *Perilla* oil; Perubalsam oil; Parsley leaf oil; Parsley seed oil; Petitgrain oil; Peppermint oil; Pepper oil; Allspice oil; Pine oil; Poley oil; Rose absolue; Rosewood oil; Rose oil; Rosemary oil; Sage oil Dalmatian; Sage oil Spanish; Sandalwood oil; Celery seed oil; Spicy lavender oil; Star anise oil; *Styrax* oil; *Tagetes* oil; Fir needle oil; Tea tree oil; Turpentine oil; Thyme oil; Tolu balsam; Tonka absolute; Tuberose absolute; Vanilla extract; Violet leaf absolute; *Verbena* oil; Vetiver oil; Juniper berry oil; Wine yeast oil; Wormwood oil; Wintergreen oil; Ylang oil; Hyssop oil; Civet absolute; Cinnamon leaf oil; Cinnamon bark oil, and fractions thereof, or ingredients isolated therefrom;

Single odorants from the group of hydrocarbons, such as 3-carene; α-pinene; α-terpinene; β-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols such as hexanol; octanol; 3-octanol; 2,6-dimethylheptanol; 2-methyl-2-heptanol; 2-methyl-2-octanol; (E)-2-hexenol; 1-octen-3-ol; Mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals, e.g. hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethyl acetal; 1,1-dimethoxy-2,2,5-trimethyl-4-hexene; citronellyloxyacetaldehyde; 1-(1-methoxy-propoxy)-(E/Z)-3-hexene;

aliphatic ketones and their oximes such as 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as 3-methylthiohexanol; 3-methylthiohexyl acetate; 3-mercaptohexanol; 3-mercaptohexyl acetate; 3-mercapto hexyl butyrate; 3-acetylthiohexyl acetate; 1-menthen-8-thiol;

aliphatic nitriles such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids, e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl-2-isoamyloxyacetate; methyl-3,7-dimethyl-2,6-octadiene-oate; 4-methyl-2-pentyl crotonate;

acyclic terpene alcohols such as e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

acyclic terpene aldehydes and ketones such as citronellal; 7-methoxy-3,7-dimethyloctanal; 2,6,10-trimethyl-9-undecenal; geranylacetone; and the dimethyl and diethylacetals of geranial, neral;

cyclic terpene alcohols such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guajol; and their formates, acetates, propionates, isobutyrates, butyrates, isovalerianates, pentanoates, hexanoates, crotonates, tiglinates and 3-methyl-2-butenoates;

cyclic terpene aldehydes and ketones, e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; beta-damascenone; 1-(2,4,4-trimethyl-2-cyclohexen-1-yl-)2-buten-1-one; 1,3,4,6,7,8a-Hexahydro-1,1,5,5-tetramethyl-2H-2,4a-methanonaphthalen-8-(5H)-on; 2-Methyl-4-(2,6,6-trimethyl-1-cyclohexen-1-yl-)2-butenal; nootkatone; dihydronootkatone; 4,6,8-megastigmatrien-3-one; alpha-sinensal; beta-sinensal; acetylated cedarwood oil (methylcedrylketone);

cyclic alcohols such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as alpha,3,3-trimethylcyclohexylmethanol; 1-(4-isopropylcyclohexyl-)ethanol; 2-methyl-4-(2,2,3-trimethyl-3-cyclopent-1-yl-)butanol; 2-methyl-4-(2,2,3-trimethyl-3-cyclopent-1-yl-)2-buten-1-ol; 3-methyl-5-(2,2,3-trimethyl-3-cyclopent-1-yl-)pentan-2-ol; 3-methyl-5-(2,2,3-trimethyl-3-cyclopent-1-yl-)4-penten-2-ol; 3,3-dimethyl-5-(2,2,3-trimethyl-3-cyclopent-1-yl-)4- penten-2-ol; 1-(2,2,6-trimethylcyclohexyl-)pentan-3-ol; 1-(2,2,6-trimethylcyclohexyl-)hexan-3-ol;

cyclic and cycloaliphatic ethers such as cineole; cedryl methyl ether; Cyclododecyl methyl ether; 1,1-dimethoxy-cyclododecane; (ethoxymethoxy) cyclo-dodecane; alpha cedrene epoxide; 3a,6,6,9a-tetramethyldodecahydro-naphtho [2,1-b] furan; 3a-ethyl-6,6,9a-trimethyldodecahydronaphtho[2,1b]furan; 1,5,9-trimethyl-13-oxabicyclo [10.1.0] tridec-4,8-diene; rose oxide; 2-(2,4-dimethyl-3-cyclohexen-1-yl-)5-methyl-5-(1-methylpropyl-)1,3-dioxane;

cyclic and macrocyclic ketones such as 4-tert-butylcyclohexanone; 2,2,5-trimethyl-5-pentylcyclopentanonebutylcyclohexanone; 2,2,5-trimethyl-5-pentylcyclopentanone; 2-heptylcyclopentanone; 2-pentyl-cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl-)3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as, for example, 2-methyl-4-(2,2,6-trimethyl-cyclohexen-1-yl-) 2-butenal; 4-(4-hydroxy-4-methylpentyl) 3-cyclohexenecarbaldehyde; 4-(4-methyl-3-penten-1-yl-)3-cyclohexenecarbaldehyde;

cycloaliphatic ketones such as 1-(3,3-dimethylcyclohexyl-)4-penten-1-on; 2,2-dimethyl-1-(2,4-dimethyl-3-cyclohexen-1-yl-)1-propanon; 1-(5,5-dimethyl-1-cyclohexen-1-yl-)4-penten-1-on; 2,3,8,8-tetramethyl-1,2,3,4,5,6,7,8-octahydro-2-naphthalenyl methyl ketone; methyl-2,6,10-trimethyl 2,5,9-cyclododecatrienyl ketone; tert.-butyl-(2,4-dimethyl-3-cyclohexen-1-yl) ketone;

esters of cyclic alcohols such as 2-tert-butyl cyclohexyl acetate; 4-tert-butyl cyclohexyl acetate; 2-tert-pentyl cyclohexyl acetate; 4-tert-pentyl cyclohexyl acetate; 3,3,5-trimethyl cyclohexyl acetate; decahydro-2-naphthyl acetate; 2-cyclo-pentylcyclopentyl crotonate; 3-pentyl tetrahydro-2H-pyran-4-yl acetate; decahydro-2,5,5,8a-tetramethyl-2-naphthyl acetate; 4,7-methano-3a,4,5,6,7,7a-hexa-hydro-5, respective, 6-indenyl acetate; 4,7-methano-3a,4,5,6,7,7a-hexahydro-5, or 6-indenyl propionate; 4,7-methano-3a,4,5, 6,7,7a-hexahydro-5, or 6-indenyl isobutyrate; 4,7-methanooctahydro-5, or 6-indenyl acetate;

esters of cycloaliphatic alcohols such as 1-cyclohexylethyl crotonate;

esters of cycloaliphatic carboxylic acids, such as allyl-3-cyclohexyl propionate; allyl cyclohexyloxy acetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

aliphatic alcohols such as benzyl alcohol; 1-phenylethyl alcohol; 3-phenyl propanol; 2-phenyl propanol; 2-phenoxyethanol; 2,2-dimethyl-3-phenyl propanol; 2,2-dimethyl-3-(3-methylphenyl) propanol; 1,1-dimethyl-2-phenylethyl alcohol; 1,1-dimethyl-3-phenylpropanol; 1-ethyl-1-methyl-3-phenyl-propanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of aliphatic alcohols and aliphatic carboxylic acids, e.g. benzyl acetate; benzyl propionate; benzyl isobutyrate; benzyl isovalerate; 2-phenylethyl acetate; 2-phenylethyl propionate; 2-phenylethyl isobutyrate; 2-phenyl ethyl isovalerate; 1-phenylethyl acetate; alpha-trichloromethyl benzyl acetate; alpha,alpha-dimethylphenyl ethyl acetate; alpha,alpha-dimethylphenyl ethyl butyrate; cinnamyl acetate; 2-phenoxyethyl isobutyrate; 4-methoxybenzyl acetate;

aliphatic ethers such as, for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetra-hydroindeno [1,2-d]-m-dioxin; 4,4a, 5,9b-tetrahydro-2,4-dimethylindeno [1,2-d]-m-dioxin;

aromatic and aliphatic aldehydes such as benzaldehyde; phenylacetaldehyde; 3-phenylpropanal; hydratropaaldehyde; 4-methylbenzaldehyde; 4-methylphenylacetaldehyde; 3-(4-ethylphenyl-)2,2-dimethylpropanal; 2-methyl-3-(4-isopropylphenyl-)propanal; 2-methyl-3-(4-isobutylphenyl-) propanal; 3-(4-tert.-butyl-phenyl-)propanal; cinnamaldehyde; alpha-butylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl-)propanal; 2-methyl-3-(4-methylenedioxyphenyl-)propanal;

of the aromatic and aliphatic ketones such as acetophenone; 4-methylacetophenone; 4-methoxyacetophenone; 4-tert.-butyl-2,6-dimethylaceto-phenone; 4-phenyl-2-butanone; 4-(4-hydroxyphenyl-)2-butanone; 1-(2-naphthalenyl-)ethanone;2-benzofuranylethanone;(3-methyl-2-benzofuranyl-) ethanone; benzophenone; 1,1,2,3,6-hexamethyl-5-indanyl methyl ketone; 6-tert.butyl-1,1-di-methyl-4-indanyl methyl ketone; 1-[2,3-dihydro-1,1,2,6-tetramethyl-3-(1-methylethyl-)1H-5-indenyl]ethanone; 5',6',7',8'-tetrahydro-3',5',6', 8',8'-hexamethyl-2-aceto-naphthone;

the aromatic and aliphatic carboxylic acids and their esters such as benzoic acid; phenylacetic acid; methyl benzoate; ethyl benzoate; hexyl benzoate; benzyl benzoate; methylphenyl acetate; ethyl phenyl acetate; geranyl phenyl acetate; phenylethyl phenyl acetate; methylcinnmat; ethyl cinnamate; benzyl cinnamate; phenylethyl cinnamate; cinnamyl cinnamate; allyl phenoxyacetate; methyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenyl glycidate; ethyl-3-methyl-3-phenyl glycidate;

nitrogen-containing aromatic compounds such as 2,4,6-trinitro-1,3-dimethyl-5-tert-butylbenzene; 3,5-dinitro-2,6-dimethyl-4-tert.butylacetophenone; cinnamic acid nitrile; 3-methyl-5-phenyl-2-pentenoic acid nitrile; 3-methyl-5-phenylpentanoic acid nitrile; methyl anthranilate; methyl N-methyl anthranilate; schiff bases of methyl anthranilate with 7-hydroxy-3,7-dimethyloctanal, 2-methyl-3-(4-tert.-butyl-phenyl-)propanal or 2,4-dimethyl-3-cyclohexenecarbaldehyde; 6-isopropylquinoline; 6-isobutylquinoline; 6-sec-butylquinoline;2-(3-phenylpropyl-)pyridine; indole; scatole; 2-methoxy-3-isopropylpyrazine; 2-isobutyl-3-methoxypyrazine;

phenols, phenyl ethers and phenyl esters such as, for example, estragole; Anethole; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl) phenol; p-cresylphenyl acetate;

heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide;4-methyl-1,4-decanolide; 1,15-pentadecanolide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; 2,3-dihydrocoumarin; octahydrocoumarin.

In a preferred embodiment, a fragrance preparation according to the invention, in particular in the form of a perfume oil, comprises one, two or more fragrance(s) according to the invention of the formulae (I), (II) or (III) with a lily of the valley odor note and optionally one or more further fragrance(s) with an odor note selected from the group consisting of floral, sweet, aqueous, powdery.

In a perfume preparation according to the invention, in particular a perfume oil, the amount of the at least one compound of the formulae (I), (II) or (III) or of its isomer as defined above is in the range from 0.0001 to 40% by weight, preferably in the range from 0.001 to 25% by weight, based on the total weight of the perfume preparation. In addition to use as a liquid in solutions or in emulsions, the compounds of the invention or fragrance preparations containing them, for example perfume oils, can be used adsorbed on solids or (micro)encapsulated in carriers. These dosage forms can provide both fine distribution of the fragrances in the product and controlled release during use. Such solids can be porous inorganic materials such as light sulfate, silica gels, zeolites, gypsums, clays, clay granules, aerated concrete, etc., or organic materials such as woods, cellulose-based materials, sugars, or plastics such as PVC, polyvinyl acetates, or polyurethanes.

Encapsulation products can, for example, be spray-dried, in the form of an inclusion complex or as an extrusion product. The microencapsulation of the perfume oils can be carried out, for example, by the so-called coacervation process using capsule materials of, for example, polyurethane-type substances or soft gelatin. The spray-dried perfume oils can be prepared, for example, by spray-drying an emulsion, or dispersion, containing the perfume oil, using modified starches, proteins, dextrin and vegetable gums as carriers. Inclusion complexes can be prepared, for example, by incorporating dispersions of the perfume oil and cyclodextrins or urea derivatives into a suitable solvent, such as water.

Extrusion products can be made by melting the perfume oils with a suitable waxy substance and by extrusion with subsequent solidification, if necessary in a suitable solvent, e.g. isopropanol.

The adsorbates as well as the encapsulation products can be further optimized by so-called coating with suitable materials with regard to a more targeted fragrance release, for which waxy plastics such as polyvinyl alcohol can preferably be used.

According to a preferred embodiment of the present invention, in perfume oil compositions which are used adsorbed on a carrier, the amount employed of the compounds of the formulae (I), (II) or (III) according to the invention or of their isomers as defined above is in the range from 0.00001 to 5% by weight, preferably in the range from 0.00001 to 1% by weight, and particularly preferably in the range from 0.0005 to 0.01% by weight, based on the total weight of the perfume oil composition.

The compounds of the invention to be used as perfumes, as defined above, and the mixtures thereof, as well as the perfume preparations of the invention, as defined above, are used in particular for the production of perfumed products.

Accordingly, the present invention also relates to perfumed products or consumer goods, including their precursors and intermediates, which comprise a fragrance compound or fragrance preparation according to the invention. A perfumed product or consumer product according to the invention comprises the compounds according to the invention as defined above, preferably in a sensory effective amount. In this context, the compound according to the invention is either used individually or is a component of a mixture or perfume preparation according to the invention.

Perfumed products or consumer goods often contain a large number of different chemical compounds. The use of the compounds according to the invention is particularly advantageous because of their low reactivity, so that neither the compounds according to the invention nor the ingredients of the consumer goods are adversely changed. In addition, the compounds according to the invention in the concentrations necessary to achieve the desired fragrance effect do not adversely affect the physical or physicochemical properties of the consumer goods (e.g., viscosity or pH).

The substances contained in perfumed products or Consumer products are often preservatives, abrasives, anti-acne agents, anti-aging agents, antibacterial agents, anti-cellulite agents, anti-dandruff agents, anti-inflammatory agents, anti-irritants, anti-irritants, antimicrobials, antioxidants, astringents, antiperspirants, antiseptics, antistatics, binders, buffers, carriers, chelating agents, cell stimulants, cleansing agents, conditioning agents, depilatories, surfactants, deodorizers, antiperspirants, emollients, emulsifiers, enzymes, essential oils, fibers, film formers, fixatives, foaming agents, foam stabilizers, anti-foaming agents, foam boosters, fungicides, gelling agents, gel-forming agents, hair care agents, hair shaping agents, hair smoothing agents, moisturizing agents, moisturizing substances, moisture-retaining substances, bleaching agents, strengthening agents, stain-removing agents, optical brightening agents, impregnating agents, soil-repellent agents, friction-reducing agents, lubricants, moisturizers, ointments, opacifiers, plasticizing agents, covering agents, polishes, brighteners, polymers, powders, proteins, refatting agents, abrasive agents, silicones, skin soothing agents, skin cleansing agents, skin caring agents, skin healing agents, skin whitening agents, skin protecting agents, skin softening agents, cooling agents, skin cooling agents, warming agents, skin warming agents, stabilizers, UV absorbing agents, UV filters, detergents, fabric softeners, suspending agents, skin tanning agents, thickening agents, vitamins, oils, waxes, fats, phospholipids, saturated fatty acids, mono- or polyunsaturated fatty acids, $\alpha$-hydroxy acids, polyhydroxy fatty acids, liquefiers, dyes, color-protecting agents, pigments, anticorrosives, aromas, flavors, fragrances, polyols, surfactants, electrolytes, organic solvents, or silicone derivatives. With these substances, the compounds according to the invention exhibit high compatibility in mixtures.

The proportion by weight of the odorant according to the invention, i.e. of the compounds according to the invention of the formulae (I), (II) or (III) or of their isomers as defined above, or of the odorant preparation according to the invention in the perfumed product or the consumer goods is 0.0001 to 5% by weight, preferably 0.001 to 2% by weight and particularly preferably 0.001 to 1%.

Perfumed products or consumer goods in the sense of the invention are detergents and cleaning agents, hygiene or care products, in particular from the field of body and hair care, cosmetics, household, fine fragrance (perfume), air care and air fresheners, in particular fabric softeners, bleaches, disinfectants, fragrance release systems, sunscreens for the skin, hair care products and deodorants. In particular, consumer products include acidic, alkaline and neutral cleaning products, such as. Floor cleaners, window glass cleaners, dishwashing detergents, bathroom and sanitary cleaners, scouring powders, solid and liquid toilet cleaners, powder and foam carpet cleaners, liquid laundry detergents, powder laundry detergents, laundry pre-treatment agents such as bleaches, soaks and stain removers, laundry softeners, laundry soaps, laundry tablets, disinfectants, surface disinfectants, and air fresheners in liquid, gel or solid carrier form including for toilet fragrancing, aerosol sprays, waxes and polishes such as furniture polishes, floor waxes, shoe polishes, and personal care products such as solid and liquid soaps, shower gels, shampoos, shaving soaps, shaving foams, bath oils, cosmetic emulsions of the oil-in-water, water-in-oil and water-in-oil-in-water type, e.g. skin creams and lotions, facial creams and lotions, sunscreen creams and lotions, after-sun creams and lotions, hand creams and lotions, foot creams and lotions, depilatory creams and lotions, after-shaves, after-shave creams and lotions, preshaves, tanning creams and lotions, hair care products such as e.g. hair sprays, hair gels, hair lotions, hair conditioners, permanent and semi-permanent hair colorants, hair shaping products such as cold waves and hair straighteners, hair tonics, hair creams and lotions, refreshing wipes, deodorants and antiperspirants such as underarm sprays, roll-ons, deodorant sticks, deodorant creams or decorative cosmetics products such as make-up.

Finally, the present invention also relates to a process for perfuming perfumed products or consumer goods, comprising adding at least one of the compounds according to the invention or the perfume preparations according to the invention to products or consumer goods to be perfumed. The advantage of the compounds according to the invention or the perfume preparations according to the invention in this method is that they can be easily incorporated into consumer goods.

The compounds of the present invention, as described above, are characterized by the fact that they impart an odor impression that largely corresponds to the complexity of the natural odor of the lily of the valley flower. Moreover, they can be produced from renewable and natural starting materials, i.e., renewable raw materials. Another advantage of the compounds according to the invention is their easy accessibility: their synthesis is based on endo-cyclic cyclohexenes instead of complexly prepared exo-cyclohexenes.

EXAMPLES

The present invention is described in more detail below with reference to examples of embodiments.

Example 1: Preparation of 2-(5-isopropyl-2-methyl-cyclohex-2-en-1-yl)acetaldehyde

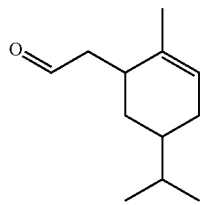

In a 1 liter double-walled vessel equipped with a head stirrer, thermostat connection, cooler and nitrogen atmosphere, 100 g of 5-isopropyl-2-methyl-cyclohex-2-en-1-ol (0.65 mol) and 0.4 g of 85% phosphoric acid are added. Then 98 g butyl vinyl ether (0.98 mol), is added in 1 to 2 hours at 35° C. Stirring is continued for 6 hours at 35° C. for the post-reaction. The mixture is washed at room temperature with 5% soda solution and then with 5% sodium chloride solution, followed by evaporation. The crude yield is 165 g.

The crude product is placed in a 500 ml three-neck flask with magnetic stirrer, 20 cm Vigreux column and distillation bridge, together with 165 g dibenzyl ether and 6.5 g caproic acid and heated at 90 mbar. At 160-175° C., the resulting light boilers are distilled off within 5 hours to a head temperature of about 80° C. The crude product is then distilled (bottom temperature: 125-170° C., top temperature: 70-110° C., vacuum: 1 mbar). 72 g are distilled off. After DB-1-GC or GCMS, 60% product is obtained as cis/trans isomers. The separation of the two isomers is carried out on a column (Fischer Column® HMS 500 AC). Boiling points at 1 mbar: 2-(5-isopropyl-2-methyl-cyclohex-2-en-1-yl)acetaldehyde: 71° C., 2-(5-isopropyl-2-methyl-cyclohex-2-en-1-yl)acetaldehyde: 73° C.

2-(5-isopropyl-2-methyl-cyclohex-2-en-1-yl)acetaldehyde: m/z: 43 (11), 55 (14), 67 (16), 81 (28), 93 (100), 109 (6), 119 (10), 136 (45), 147 (1), 180 (5).

Odor description: Aldehydic, floral lily of the valley, green.

2-(5-isopropyl-2-methyl-cyclohex-2-en-1-yl)acetaldehyde: m/z: 43 (13), 55 (17), 67 (21), 81 (33), 93 (100), 109 (9), 119 (13), 136 (55), 147 (2), 180 (4).

Odor description: green, floral lily of the valley, aldehydic.

Example 2: Preparation of 2-(6-isopropyl-3-methyl-cyclohex-2-en-1-yl)acetaldehyde

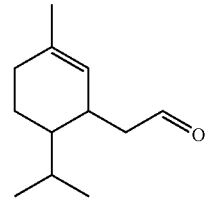

In a 2 liter stirrer 122 g (0.8 mol) piperitone and 700 ml methanol are added. At 0-5° C., 80 g of 25% (0.5 mol) sodium hydroxide solution are slowly added. The temperature rises to about 20° C. Under slight cooling, 181 g of 30-% (1.6 mol) hydrogen peroxide is added in 1 h, at 28-33° C. Subsequently, stirring is continued for another 6 h at 28° C. Then pour to 1000 ml of water and extract twice with 300 ml of MTBE each. The MTBE phases are combined and washed successively with water, 10% potassium iodide solution and water to remove peroxide, and then evaporated. 130 g of crude product is obtained. According to GC/GCMS, trans-piperitone epoxide and cis-piperitone epoxide are present in a ratio of 1:3.5.

The crude product is placed in a 2 liter stirrer together with 500 ml methanol and 50 g (1 mol) of hydrazine monohydrate is added at 0-5° C. The product is then stirred until it reaches the desired temperature. The temperature is increased to 17-20° C. Under cooling and nitrogen evolution, 60 g (1 mol) acetic acid is added in 30 min at 20-25° C. Stirring is continued for 2 h. The mixture is poured onto 1500 ml water and then extracted twice with 500 ml MTBE each. The MTBE phases are combined and washed successively with water and saturated sodium bicarbonate and then evaporated. 99 g of crude product is obtained. According to GC/GCMS, trans-4-isopropyl-1-methyl-cyclohex-2-en-1-ol and cis-4-isopropyl-1-methyl-cyclohex-2-en-1-ol are present in a ratio of 1:3.5. Distillation on a 30 cm packed column at a boiling point of 85-102° C., at 14 mbar, yields 26 g of a fraction containing 19% trans-4-isopropyl-1-methyl-cyclohex-2-en-1-ol and 67% cis-4-isopropyl-1-methyl-cyclohex-2-en-1-ol by GC/GCMS.

The distillate (26 g) is placed in a 0.1 liter double-walled vessel with magnetic stirrer, thermostat connection, cooler and nitrogen atmosphere together with 0.1 g 85% phosphoric acid. Then 22 g (0.22 mol) of butyl vinyl ether is added in 1 to 2 hours at 35° C. Stirring is continued for 2 hours at 35° C. for post-reaction. The mixture is washed at room temperature with 5% soda solution and then with 5% sodium chloride solution, followed by evaporation at 60° C. and 700 to 5 mbar on a rotary evaporator. The yield is 31.3 g.

30 g of the crude product are placed in a 250 ml three-neck flask with magnetic stirrer, 20 cm Vigreux column and distillation bridge together with 30 g dibenzyl ether, and 1.5 g caproic acid and heated at 90 mbar. At 160-175° C., the resulting light boilers are distilled off within 3 hours to a head temperature of approx. 80° C. The crude product is then distilled off. The crude product is then distilled (bottom temperature: 125-170° C., top temperature: 65-90° C., vacuum: 1 mbar). 10 g are distilled off.

After DB-1-GC or GCMS, 60% product (cis/trans isomers) was obtained.
m/z: 43 (17), 55 (23), 67 (36), 81 (100), 93 (77), 110 (19), 119 (18), 136 (47), 165 (13), 180 (14).
Description of odor: Aldehydic, green, floral, lily of the valley.
m/z: 43 (19), 55 (27), 67 (40), 81 (100), 93 (95), 110 (24), 119 (21), 136 (51), 165 (15), 180 (13)
Odor description: Green, aldehydic, floral, lily of the valley.

Design Example 3: Perfume Oil A

Composition of the perfume oil A1 or A2:

| Fragrances | Weight parts | |
|---|---|---|
| | Perfume oil A1 (comparison) | Perfume oil A2 (according to the invention) |
| ETHYL ACETOACETATE | 4.0 | 4.0 |
| HEXENOL CIS-3 10% DPG | 3.0 | 3.0 |
| HEXENYL ACETATE CIS-3 10% DPG | 3.0 | 3.0 |
| HEXENYL BENZOATE CIS-3 10% DPG | 3.0 | 3.0 |
| VERTOCITRAL 10% DPG | 5.0 | 5.0 |
| CYCLOGALBANATE ® 10% DPG | 3.0 | 3.0 |
| STYRALYL ACETATE 10% DPG | 6.0 | 6.0 |
| BERGAMOT OIL BERGAPTEN FREE FF | 6.0 | 6.0 |
| MANDARIN OIL DIST. DECOL. | 15.0 | 15.0 |
| METHYL ANTHRANILATE 10% DPG | 5.0 | 5.0 |
| RED BERRY EXTR. | 2.0 | 2.0 |
| DECALACTONE GAMMA | 2.0 | 2.0 |
| ALLYL CAPROATE 10% DPG | 5.0 | 5.0 |
| PRUNELLA TYPE BASE | 6.0 | 6.0 |
| HELIONAL | 20.0 | 20.0 |
| MUGETANOL | 10.0 | 10.0 |
| ETHYL LINALOOL | 35.0 | 35.0 |
| CITRONELLOL 950 | 10.0 | 10.0 |
| GERANIOL SUPER | 3.0 | 3.0 |
| ROSAPHEN ® | 8.0 | 8.0 |
| CITRONELLYL ACETATE EXTRA | 2.0 | 2.0 |
| DAMASCONE BETA 10% DPG | 6.0 | 6.0 |
| BENZYL ACETATE | 10.0 | 10.0 |
| HEDION HC/30 | 30.0 | 30.0 |
| HEDIONE | 140.0 | 140.0 |
| HEXYL CINNAMIC ALDEHYDE ALPHA | 30.0 | 30.0 |
| LACTOJASMONE | 3.0 | 3.0 |
| BENZYL SALICYLATE | 80.0 | 80.0 |
| HEXENYL SALICYLATE CIS-3 | 30.0 | 30.0 |
| METHYL IONONE GAMMA COEUR | 3.0 | 3.0 |
| CLOVE BUD OIL | 1.0 | 1.0 |
| VANILLIN | 1.5 | 1.5 |
| COUMARIN | 1.0 | 1.0 |
| AMBERWOOD ® F | 5.0 | 5.0 |
| CASHMERAN | 8.0 | 8.0 |
| CEDRENE | 15.0 | 15.0 |
| ISO E SUPER NON DISCOLORING | 50.0 | 50.0 |
| BRAHMANOL ® | 25.0 | 25.0 |
| SANDALORE | 5.0 | 5.0 |
| AMBROXIDE | 2.0 | 2.0 |
| AMBRETTOLIDE | 5.0 | 5.0 |
| AURELIONE ® | 16.0 | 16.0 |
| GLOBALIDE ® | 24.0 | 24.0 |
| MACROLIDE ® SUPRA | 16.0 | 16.0 |
| INDOLE FF 10% DPG | 5.0 | 5.0 |
| 2-(5-isopropyl-2-methyl-cyclohex-2-en-1-yl)acetaldehyde | | 50.0 |
| DIPROPYLENE GLYCOL | 332.5 | 282.5 |
| | 1000.0 | 1000.0 |

At a dosage of 6% by weight of perfume oil A1 and A2, respectively, the following finding is obtained: compared to perfume oil A1, the addition of 2-(5-isopropyl-2-methyl-cyclohex-2-en-1-yl)acetaldehyde in perfume oil A2 enhances floral aspects.

Example of Execution 4: Perfume Oil B

Composition of perfume oil B1 or B2:

| Fragrances | Weight parts | |
|---|---|---|
| | Perfume oil B1 (comparison) | Perfume oil B2 (according to the invention) |
| NONADIENAL TRANS,CIS-2,6 5% TEC 20% DPG | 2.0 | 2.0 |
| ETHYL ACETOACETATE | 3.0 | 3.0 |
| FARENAL ® 10% DPG | 5.0 | 5.0 |
| VERTOCITRAL | 3.0 | 3.0 |
| CYCLOGALBANATE 10% DPG | 2.0 | 2.0 |
| STYRALYL ACETATE | 3.0 | 3.0 |
| MELONAL ® | 0.5 | 0.5 |
| DIHYDRO MYRCENOL | 15.0 | 15.0 |

| Fragrances | Perfume oil B1 (comparison) | Perfume oil B2 (according to the invention) |
|---|---|---|
| LINALYL ACETATE | 20.0 | 20.0 |
| LEMON OIL TERPENES FLAVOR WONF | 8.0 | 8.0 |
| EUCALYPTOL NAT. 10% DPG | 0.5 | 0.5 |
| HEXYL ACETATE | 1.5 | 1.5 |
| ISOAMYL ACETATE 10% DPG | 4.0 | 4.0 |
| PRENYL ACETATE 10% DPG | 4.0 | 4.0 |
| ALDEHYDE C14 SO-CALLED | 2.0 | 2.0 |
| ETHYL METHYL BUTYRATE-2 | 1.0 | 1.0 |
| ALLYL CYCLOHEXYL PROPIONATE | 2.0 | 2.0 |
| ALDEHYDE C16 SO-CALLED | 1.0 | 1.0 |
| FRAGOLANE ® | 0.5 | 0.5 |
| MAJANTOL ® | 25.0 | 25.0 |
| LINALOOL | 40.0 | 40.0 |
| DIMETHYL BENZYL CARBINOL | 10.0 | 10.0 |
| TERPINEOL PURE | 10.0 | 10.0 |
| PHENIRATE ® | 30.0 | 30.0 |
| CITRONELLOL 950 | 15.0 | 15.0 |
| GERANIOL 60 | 10.0 | 10.0 |
| CITRONELLYL ACETATE | 2.0 | 2.0 |
| EXTRA HEDIONE | 90.0 | 90.0 |
| HEXYL CINNAMIC ALDEHYDE ALPHA | 35.0 | 35.0 |
| HEXYL SALICYLATE | 160.0 | 160.0 |
| METHYL OCTIN CARBONATE 10% DPG | 2.0 | 2.0 |
| CALONE 1951 10% DPG | 1.0 | 1.0 |
| GALAXOLIDE 50% IN IPM | 20.0 | 20.0 |
| ANETHOLE SUPRA 21.5 CELSIUS | 2.0 | 2.0 |
| AGRUMEX HC | 15.0 | 15.0 |
| ORYCLON SPECIAL | 40.0 | 40.0 |
| 2-(6-Isopropyl-3-methyl-cyclohex-2-en-1-yl)acetaldehyde | | 15.0 |
| DIPROPYLENE GLYCOL | 415.0 | 400.0 |
| | 1000.0 | 1000.0 |

At a dosage of 0.5% by weight of perfume oil B1 or B2, the following finding is obtained: due to the proportion of 2-(6-isopropyl-3-methyl-cyclohex-2-en-1-yl)acetaldehyde, perfume oil B2 exhibits a stronger floral note than perfume oil B1 without 2-(6-isopropyl-3-methyl-cyclohex-2-en-1-yl) acetaldehyde. Furthermore, perfume oil B2 shows a greener top note than perfume oil B1.

The invention claimed is:

1. A compound according to formula (II) or formula (III):

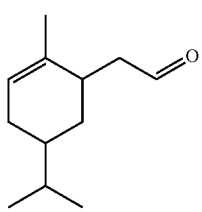

(II)

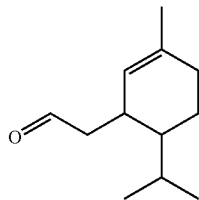

(III)

or a stereoisomer thereof, or a mixture thereof, wherein the compound according to formula (II) or formula (III), or stereoisomer thereof or mixture thereof exhibits a lily of the valley odor note.

2. A compound according to claim 1, wherein the compound of formula (II) is represented by the following formula (IIa) or formula (IIb):

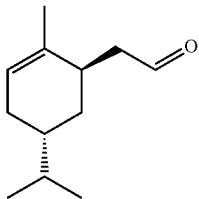

(IIa)

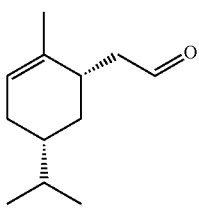

(IIb)

or a mixture thereof.

3. A compound according to claim 1, wherein the compound of formula (III) is represented by the following formula (IIIa) or formula (IIIb):

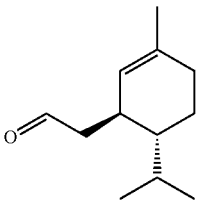

(IIIa)

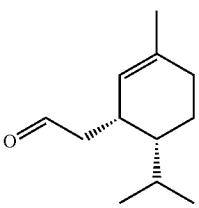

(IIIb)

or a mixture thereof.

4. A mixture comprising (a) at least one compound of formula (II) or a stereoisomer thereof, and (b) at least one compound of formula (III) or a stereoisomer thereof according to claim 1.

5. A process for preparing a compound of formula (II) according to claim 1, comprising the following steps:
   (i) acid reaction of the compound 2-methyl-5-(1-methylethyl-)2-cyclohexen-1-ol (IV) with at least one vinyl ether (R-O) to give an acetal (V);
   (ii) cleavage of the acetal (V) obtained in step (i) by acid catalysis into a vinyl ether (VI); and
   (iii) thermal conversion of the vinyl ether (VI) obtained in step (ii) into the aldehyde (II);
   according to the following reaction scheme:

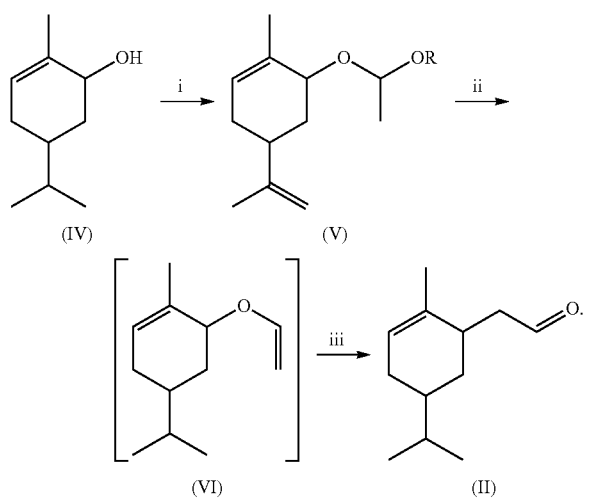

6. A process for preparing a compound of formula (II) according to claim 5, wherein the radical R of the vinyl ether (R-O) in step (i) is selected from the group consisting of linear C1 to C20 alkyl radical, branched C1 to C20 alkyl radical, cyclopentyl radical and cyclohexyl radical.

7. A process for preparing a compound of formula (II) according to claim 1, comprising the following steps:
   (i) acid reaction of the compound 2-methyl-5-(1-methylethenyl-)2-cyclohexen-1-ol (VII) with at least one vinyl ether (R-O) to give an acetal (VIII);
   (ii) cleavage of the acetal (VIII) obtained in step (iv) by acid catalysis into a vinyl ether (IX);
   (iii) thermal conversion of the vinyl ether (IX) obtained in step (v) into the aldehyde (X); and
   (iv) hydrogenation of the terminal double bond to give the aldehyde (II);
   according to the following reaction scheme:

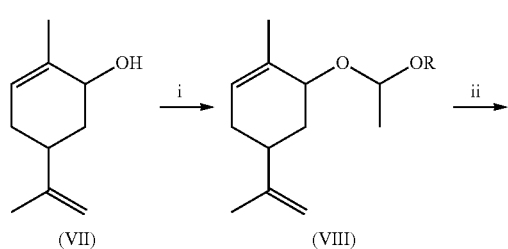

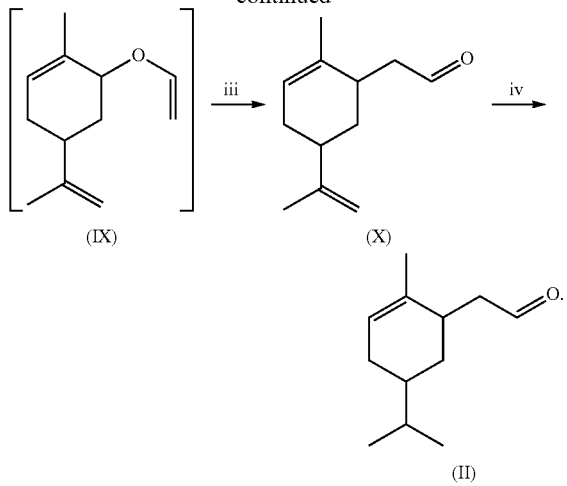

8. A process for preparing a compound of formula (III) according to claim 1, comprising the following steps:
   (i) acid reaction of the compound 1-methyl-4-(1-methylethyl-)2-cyclohexen-1-ol (XI) with at least one vinyl ether (R-O) to give an acetal (XII);
   (ii) cleaving the acetal (XII) obtained in step (vii) by acid catalysis into a vinyl ether (XIII); and
   (iii) thermal conversion of the vinyl ether (XIII) obtained in step (viii) into the aldehyde (III);
   according to the following reaction scheme:

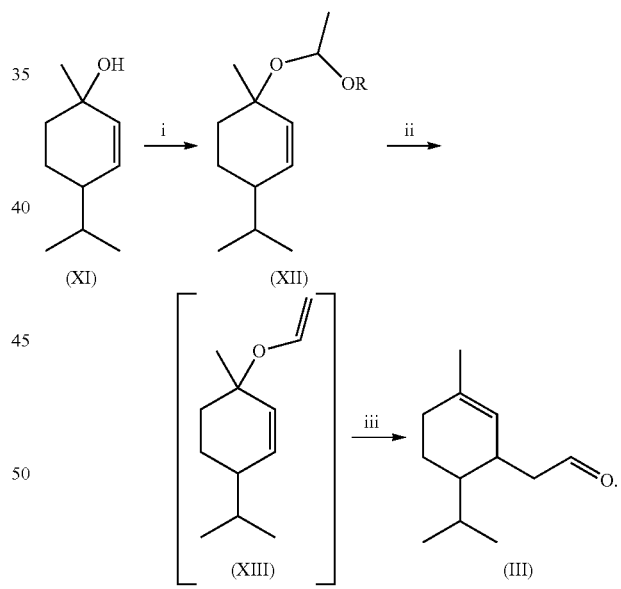

9. A process for preparing a compound of formula (III) according to claim 8, wherein the radical R of the vinyl ether (R-O) in step (i) is selected from the group consisting of linear C1 to C20 alkyl radical, branched C1 to C20 alkyl radical, cyclopentyl radical and cyclohexyl radical.

10. A process for preparing a compound of formula (III) according to claim 1, comprising the following steps:
    (i) acid reaction of the compound 1-methyl-4-(1-methylethenyl-)2-cyclohexen-1-ol (XX) with at least one vinyl ether (R-O) to give an acetal (XXI);
    (ii) cleavage of the acetal (XXI) obtained in step (vii) by acid catalysis into a vinyl ether (XXII);

(iii) thermal conversion of the vinyl ether (XXII) obtained in step (viii) into the aldehyde (XXIII); and
(iv) hydrogenation of the terminal double bond to give the aldehyde (III);
according to the following reaction scheme:

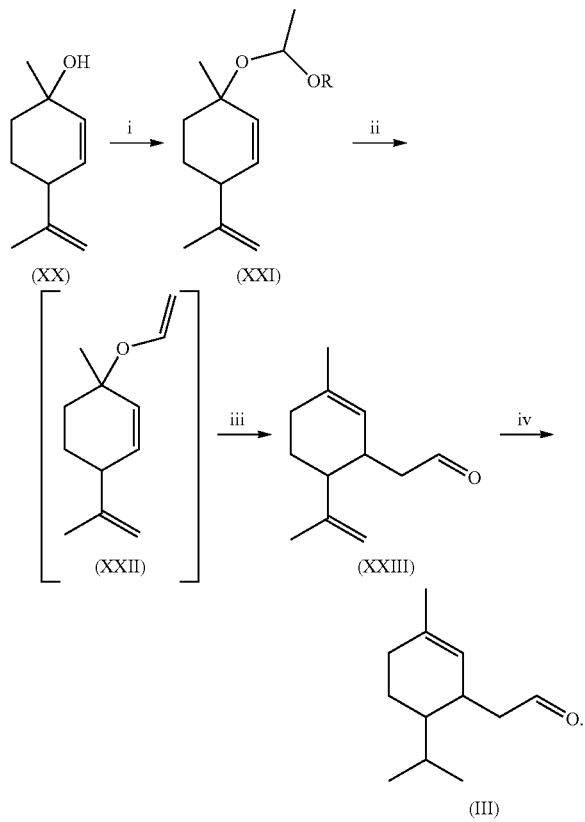

11. A method of using at least one compound according to claim 1, comprising using the compound as a perfume or for the preparation of a perfume composition.

12. A perfume or perfume preparation comprising at least one compound of formula (II) and/or (III) or a stereoisomer thereof according to claim 1.

13. A perfume preparation according to claim 12, further comprising one or more additional perfume(s) and/or aroma(s), wherein said one or more additional perfume(s) and/or aroma(s) is/are selected from one or more in the group of: extracts of natural raw materials, preferably essential oils, concretes, absolues, resins, resinoids, balsams, tinctures and/or single odorants, preferably from the group of hydrocarbons, aliphatic alcohols, aliphatic aldehydes and their acetals, aliphatic ketones and their oximes, aliphatic sulfur-containing compounds, aliphatic nitriles, esters of aliphatic carboxylic acids, acyclic terpene alcohols, acyclic terpene aldehydes and ketones, cyclic terpene alcohols, cyclic terpene aldehydes and ketones, cyclic alcohols, cycloaliphatic alcohols, cyclic and cycloaliphatic ethers, cyclic and macrocyclic ketones, cycloaliphatic aldehydes, cycloaliphatic ketones, esters of cyclic alcohols, esters of cycloaliphatic alcohols, aliphatic alcohols, esters of aliphatic alcohols and aliphatic carboxylic acids, aliphatic ethers, aromatic and aliphatic aldehydes, aromatic and aliphatic ketones, aromatic and aliphatic carboxylic acids and their esters, nitrogen-containing aromatic compounds, phenols, phenyl ethers and phenyl esters, heterocyclic compounds, and lactones.

14. The perfume preparation according to claim 12, wherein the total amount of the one or more compounds of formula (II) and/or (III) according to claim 2 is 0.00001 to 5% by weight, based on the total weight of the perfume preparation.

15. A perfumed product comprising a fragrance or a fragrance preparation according to claim 12, and a supplement.

16. A perfumed product according to claim 15, comprising one or more additives selected from the group of: preservatives, abrasives, anti-acne agents, anti-aging agents, antibacterial agents, anti-cellulitis agents, anti-dandruff agents, anti-inflammatory agents, anti-irritant agents, anti-irritant agents, antimicrobial agents, antioxidants, astringents, antiperspirants, antiseptics, antistatics, binders, buffers, carriers, chelating agents, cell stimulants, cleansing agents, conditioning agents, depilatories, surfactants, deodorizers, antiperspirants, emollients, emulsifiers, enzymes, essential oils, fibers, film formers, fixatives, foaming agents, foam stabilizers, anti-foaming substances, foam boosters, fungicides, gelling agents, gelling agents, hair care agents, hair shaping agents, hair smoothing agents, moisturizing agents, moistening substances, moisture retaining substances, bleaching agents, strengthening agents, stain removing agents, optical brightening agents, impregnating agents, soil-repellent agents, friction-reducing agents, lubricants, moisturizers, ointments, opacifiers, plasticizing agents, covering agents, polishes, brighteners, polymers, powders, proteins, refatting agents, abrasive agents, silicones, skin soothing agents, skin cleansing agents, skin conditioning agents, skin healing agents, skin whitening agents, skin protecting agents, skin softening agents, cooling agents, skin cooling agents, warming agents, skin warming agents, stabilizers, UV absorbing agents, UV filters, detergents, fabric softeners, suspending agents, skin tanning agents, -thickening agents, vitamins, oils, waxes, fats, phospholipids, saturated fatty acids, mono- or polyunsaturated fatty acids, a-hydroxy acids, polyhydroxy fatty acids, liquefiers, dyes, color-protecting agents, pigments, anti-corrosives, aromas, flavors, fragrances, polyols, surfactants, electrolytes, organic solvents or silicone derivatives.

17. The perfumed product according to claim 15, wherein the product is one selected from the group consisting of: detergents and cleaning products, hygiene or care products, especially in the field of body and hair care, cosmetics, of the household, fine fragrances (perfumes), air care and air fresheners.

18. The perfume preparation according to claim 12, wherein the total amount of the one or more compounds of formula (II) and/or formula (III) is 0.00001 to 1% by weight, based on the total weight of the perfume preparation.

19. A compound according to claim 1, wherein the compound of formula (II) or formula (III) is a diastereomer thereof.

20. A compound according to claim 1, wherein the compound of formula (II) or formula (III) is an enantiomer thereof.

* * * * *

UNITED STATES PATENT AND TRADEMARK OFFICE
CERTIFICATE OF CORRECTION

PATENT NO.       : 11,420,921 B2
APPLICATION NO.  : 17/276442
DATED            : August 23, 2022
INVENTOR(S)      : Bernd Hoelscher et al.

Page 1 of 1

It is certified that error appears in the above-identified patent and that said Letters Patent is hereby corrected as shown below:

On the Title Page

Item (54), and in the Specification, Column 1, Line 4, "EN-1-YL-) ACETALDEHYDE" should be
-- EN-1-YL-)ACETALDEHYDE --.

In the Claims

At Column 23, Lines 14-22, " 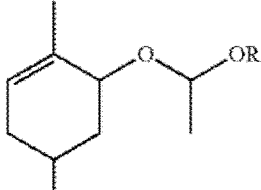 " should be -- 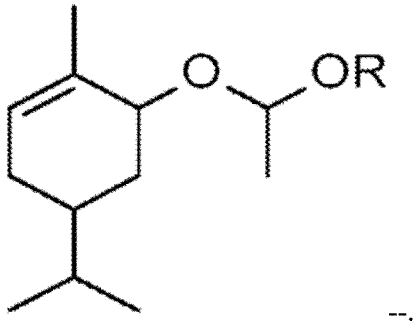 --.

At Column 26, Line 43, "a-hydroxy" should be -- α-hydroxy --.

Signed and Sealed this
Twenty-first Day of February, 2023

Katherine Kelly Vidal
*Director of the United States Patent and Trademark Office*